(12) United States Patent
Lin et al.

(10) Patent No.: US 8,477,153 B2
(45) Date of Patent: Jul. 2, 2013

(54) METHOD AND SYSTEM FOR NAVIGATING, SEGMENTING, AND EXTRACTING A THREE-DIMENSIONAL IMAGE

(75) Inventors: Zhongmin Lin, Waukesha, WI (US); Gopal Avinash, Waukesha, WI (US); Patrick Michael Virtue, Albany, CA (US)

(73) Assignee: General Electric Company, Schenectady, NY (US)

( * ) Notice: Subject to any disclaimer, the term of this patent is extended or adjusted under 35 U.S.C. 154(b) by 4 days.

(21) Appl. No.: 13/217,082

(22) Filed: Aug. 24, 2011

(65) Prior Publication Data

US 2013/0050208 A1 Feb. 28, 2013

(51) Int. Cl.
*G09G 5/00* (2006.01)
*G06T 15/00* (2011.01)

(52) U.S. Cl.
USPC .......................................... 345/624; 345/419

(58) Field of Classification Search
None
See application file for complete search history.

(56) References Cited

U.S. PATENT DOCUMENTS

2009/0190811 A1* 7/2009 Zheng et al. .................. 382/128
2012/0189185 A1* 7/2012 Chen et al. .................... 382/131

FOREIGN PATENT DOCUMENTS

| EP | 1750226 | 2/2007 |
|----|---------|--------|
| WO | 2005038711 | 4/2005 |
| WO | 2005078666 | 8/2005 |
| WO | 2006056614 | 6/2006 |
| WO | 2009111753 | 9/2009 |
| WO | 2010113051 | 10/2010 |

OTHER PUBLICATIONS

Carlson; Surface Wrapping: A Deformable Mesh Approach to Semi-Automatic 3D Volume Segmentation; Proquest Dec. 2010.*
Gamedev.net; Point inside Mesh; http://www.gamedev.net/topic/442630-point-inside-mesh/; dated Apr. 2007; retrieved Nov. 2, 2012.*
Konstantin Levinski et al; "Interactive surface-guided segmentation of brain MRI data", Computers in Biology and Medicine 39 (2009) 1153-1160; (c) 2009 Elsevier Ltd. All rights reserved.
Konstantin Levinski et al; "3D Visualization and Segmentation of Brain MRI Data"; GRAPP 2009—International Conference on Computer Graphics Theory and Applications; 8pgs.
Search Report and Written Opinion from corresponding PCT Application No. PCT/US2012/043224 dated Oct. 22, 2012.
Allan J. B. et al, "A Methodology for Direct Manipulationof Polygon Meshes", New Advances in Computer Graphics, Proceedings of CG International pp. 451-469, Jun. 27, 1989.
Olabarraga, S. D. et al, "Interaction in the segmentation of medical images: A Survey", Medical Image Analysis, Oxford University Press vol. 5 No. 2, pp, 127-142, Jun. 13, 2001.
Marcel, Jackowski, et al, "A Computer-Aided Design System for Revision of Segmentation Errors", Medical Image Computing and Computer-Assisted Intervention, pp. 717-724, Jan. 1, 2005.
Bornik, A., et al, "Interactive Editing of Segmented Volumetric Datasets in a Hybrid 2D/3D Virtual Enviroment", VRST 06 ACM Symposium on Virtual Reality Software & Technology, pp. 197-206, Nov. 1, 2006.
Schwarz, Tobias, et al, "Interactive Surface Correction for 3D Shape based Segmentation", Medical Imaging 2008: Image Processing vol. 6914, 99. 1-8 Jan. 1, 2008.

* cited by examiner

*Primary Examiner* — Carlos Perromat
(74) *Attorney, Agent, or Firm* — The Small Patent Law Group; Dean D. Small

(57) ABSTRACT

A method for extracting a three-dimensional (3D) volume of interest from a three-dimensional (3D) image dataset includes accessing a 3D image dataset that includes a plurality of image slices, enclosing a 3D volume of interest in the 3D image dataset using a 3D mesh, automatically extracting the 3D volume of interest based on the 3D mesh, and generating a 3D image of the extracted 3D volume of interest. A computer and a non-transitory computer readable medium are also described herein.

20 Claims, 15 Drawing Sheets

METHOD AND SYSTEM FOR NAVIGATING, SEGMENTING, AND EXTRACTING A THREE-DIMENSIONAL IMAGE

BACKGROUND OF THE INVENTION

The subject matter described herein relates generally to processing three-dimensional (3D) imaging datasets, and more particularly, to a method and apparatus for navigating, segmenting, and extracting a 3D image dataset.

Automated segmentation methods are commonly used to outline objects in volumetric image data. Various methods are known that are suitable for 3D segmentation. Most of the segmentation methods rely upon deforming an elastic model towards an edge or edges in the volumetric image data. Accurate segmentation of large quantities of images in a clinical application is often difficult to accomplish because of the complex and varied anatomy of the patient, image inhomogeneity, partial volume effect, and/or motion related imaging artifacts. As a result, automatic image segmentation algorithms are typically adjusted using manual editing techniques implemented by the operator. Manual editing is typically performed on a slice-by-slice and a pixel-by-pixel basis after the automatic segmentation algorithm is completed. Thus, because a 3D image dataset may include thousands of 2D slices, the time required for an operator to perform manual editing is often time consuming.

Moreover, manual editing of the segmentation results is often difficult when the segmentations results must have adequate precision to support clinical decision making. Therefore, because manually editing of the segmentation results is often time consuming, medical imaging applications that do not include highly accurate automatic image segmentation algorithms may not be useful in a clinical setting.

BRIEF DESCRIPTION OF THE INVENTION

In one embodiment, a method for extracting a three-dimensional (3D) volume of interest from a three-dimensional (3D) image dataset is provided. The method includes accessing a 3D image dataset that includes a plurality of image slices, enclosing a 3D volume of interest in the 3D image dataset using a 3D mesh, automatically extracting the 3D volume of interest based on the 3D mesh, and generating a 3D image of the extracted 3D volume of interest. A computer and a non-transitory computer readable medium are also described herein.

In another embodiment, a system for extracting a three-dimensional (3D) volume of interest from a three-dimensional (3D) image is provided. The system includes a user interface and a processor coupled to the user interface. The processor is configured to access a 3D image dataset that includes a plurality of image slices, enclose a 3D volume of interest in the 3D image dataset using a 3D mesh, automatically extract the 3D volume of interest based on the 3D mesh, and generate a 3D image of the extracted 3D volume of interest.

In a further embodiment, a non-transitory computer readable medium is provided. The computer readable medium is programmed to instruct a computer to access a 3D image dataset that includes a plurality of image slices, enclose a 3D volume of interest in the 3D image dataset using a 3D mesh, automatically extract the 3D volume of interest based on the 3D mesh, and generate a 3D image of the extracted 3D volume of interest.

DETAILED DESCRIPTION OF THE INVENTION

Figure 1:
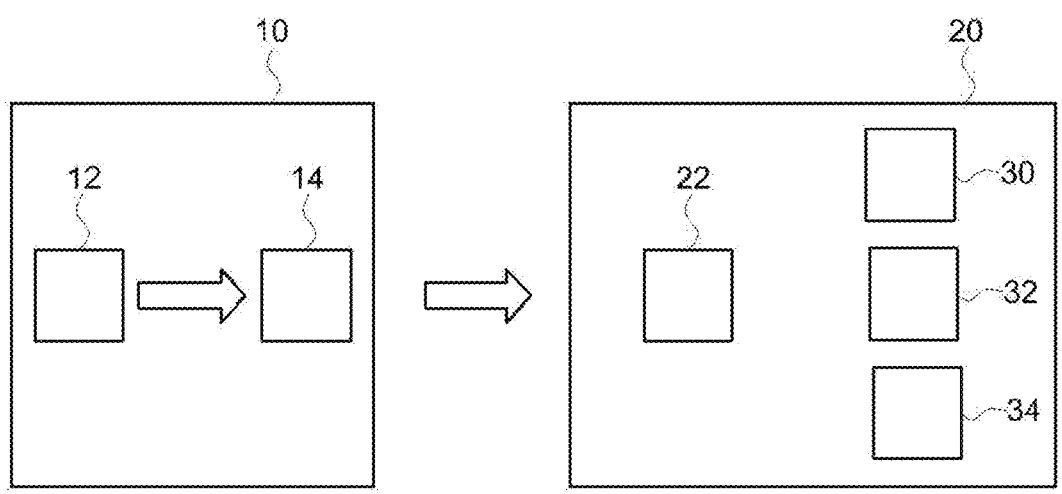
FIG. 1 is a simplified block diagram of an exemplary imaging system formed in accordance with various embodiments.

Embodiments of the invention will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide systems and methods for navigating a three-dimensional (3D) image, methods for generating a 3D mesh, and methods for extracting a 3D volume of interest. Specifically, various embodiments access a 3D image dataset, generate a 3D mesh corresponding to a 3D segmentation result using the 3D image dataset, display a 3D surface rendering for the 3D surface mesh, and enable an operator to navigate the 3D image based on a manual input received from a user indicated on the rendered 3D mesh. Thus, by practicing various embodiments, one technical effect is reduced time utilized to render, segment, and/or extract, a 3D image.

FIG. 1 is a simplified block diagram of an exemplary imaging system 10 that is formed in accordance with various embodiments. In the exemplary embodiment, the imaging system 10 is a MM system. In operation, the system 10 is configured to induce a population of spins into a subject 12 to produce a set of nuclear magnetic resonance (NMR) signals that represent a three-dimensional (3D) image dataset 14 of at least a portion of the subject 12. The imaging system 10 also includes a computer 20 that receives the 3D image dataset 14. The computer 20 processes the 3D image dataset 14 to reconstruct a 3D image 22 of an area of interest of the subject 12. In various embodiments, the computer 20 may include a 3D image navigation module 30 that is programmed to enable an operator to navigate the 3D image 22 based on a manual input received from an operator. The computer 20 may also include a segmentation module 32 that is programmed to segment the 3D image dataset 14 to generate a segmented 3D image 22. The computer 20 may further include an object extraction module 34 that is programmed to extract a 3D image of an exemplary object or organ (not shown) from the 3D image dataset 14. It should be noted that the modules 30, 32, and 34 may be implemented in hardware, software, or a combination thereof. For example, the modules 30, 32, and 34 may be implemented as, or performed, using tangible non-transitory computer readable medium.

Figure 2:
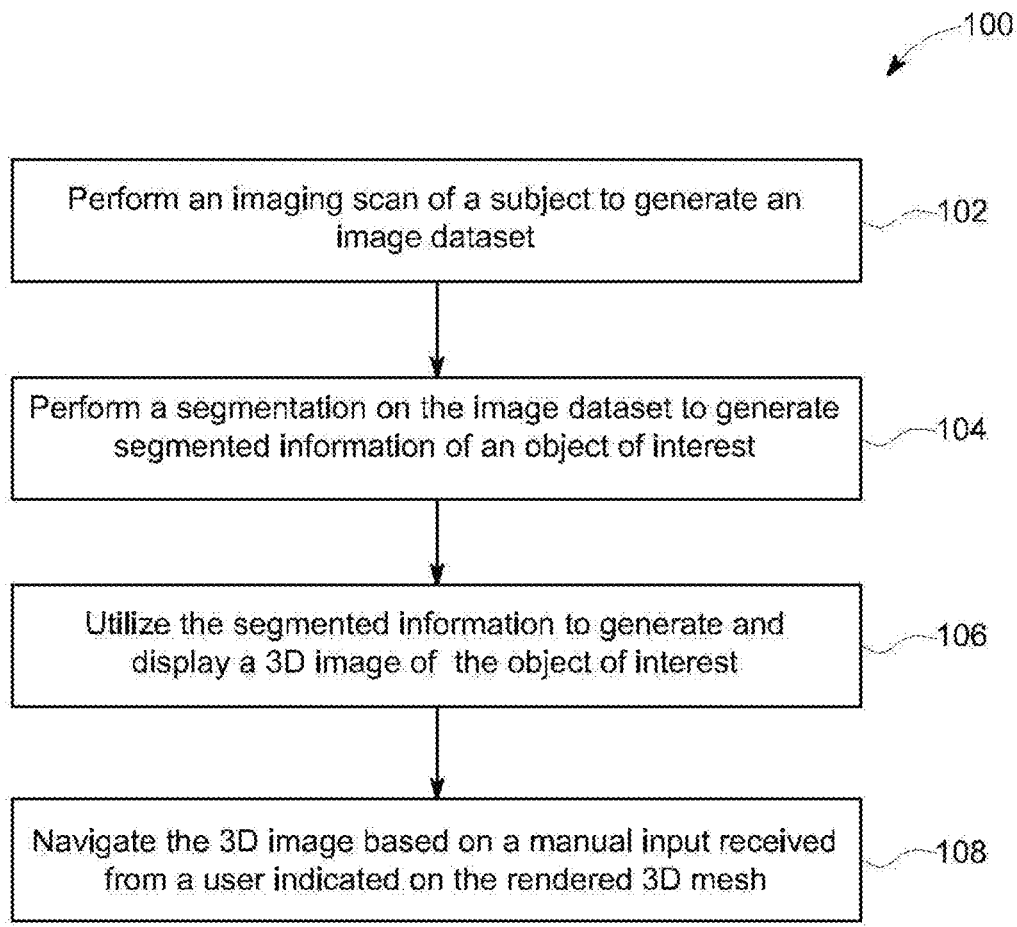
FIG. 2 is a flowchart illustrating an exemplary method of navigating a three-dimensional (3D) image in accordance with various embodiments.

FIG. 2 is a flowchart of an exemplary method 100 for navigating a 3D image utilizing an imaging system, such as the imaging system 10 shown in FIG. 1. In the exemplary embodiment, image navigation is performed by the 3D image navigation module 30 based on a manual input received from the operator. However, it should be realized that the various embodiments of navigating the 3D image may be implemented using any imaging system and the imaging system 10 shown in FIG. 1 is one embodiment of such an exemplary imaging system. The method 100 may be embodied as a set of instructions that are stored on the computer 20 and/or the navigation module 30, for example.

At 102, an imaging scan of the subject 12 is performed to generate the raw image dataset 14, also referred to herein, as a 3D volumetric dataset. More specifically, the imaging system 10 performs a scan to generate the NMR signals. In the exemplary embodiment, the imaging system 10 is configured to perform a scan of a region of interest that includes, for example, the brain. Accordingly, the 3D image dataset 14 is a set of 3D data that is represented by three orthogonal axes acquired over a predetermined time period of the brain and at least some of the regions surrounding the brain. The 3D image dataset 14 is representative of NMR signals of the region of interest including the brain. It should be realized that although various embodiments are described with respect to imaging a brain, the various embodiments may also be utilized to image other organs and the brain is an example of one such organ.

At 104, a segmentation algorithm is performed on the 3D image dataset 14 to separate image data related to the brain from image data related to other anatomical features. In operation, the segmentation algorithm is configured to locate objects of interest, such as the brain, and separate image data of the brain from image data of surrounding objects of lesser or no interest (e.g. lower clinical relevance).

The segmentation algorithm uses a principle, whereby it is generally assumed that bones and fluid surrounding the brain, and other anatomical features, may be differentiated from the brain by determining the density of each voxel in the image data. The density generally represents the intensity value of the voxel. Based on the density values of each of the voxels, the brain may be distinguished from the other anatomical features. Accordingly, at 104 the segmentation algorithm utilizes a surface mesh (discussed in more detail below) to automatically compare the density value for each voxel in the image dataset 14 to a predetermined density value, using for example, a thresholding process. In the exemplary embodiment, the predetermined density value may be a range of predetermined density values. The predetermined density value range may be automatically set based on a priori information of the brain. Optionally, the predetermined range may be manually input by the operator. In one embodiment, if the density value of a voxel is within the predetermined range, the voxel is classified as belonging to the brain. Otherwise, the voxel is classified as not belonging to the brain. It should be realized that the segmentation algorithm may also be utilized with other segmentation techniques to identify the brain. Additionally, as should be appreciated, other suitable segmentation algorithms may be used.

Accordingly, at 104 the image data in the image dataset 14 of the brain, for example, voxel information that is identified using the segmentation algorithm, is utilized to generate a dataset that includes voxel information representing the brain. Separating the voxel information by removing data that is not of interest (e.g., substantially everything that is external to the brain) from the original image dataset 14, facilitates reducing the number of voxels remaining to be processed. In the exemplary embodiment, the segmentation described at 104 is implemented using a 3D mesh 214 (shown in FIGS. 5-7). The 3D mesh 214 may be a seed algorithm or other suitable algorithm.

Figure 3:
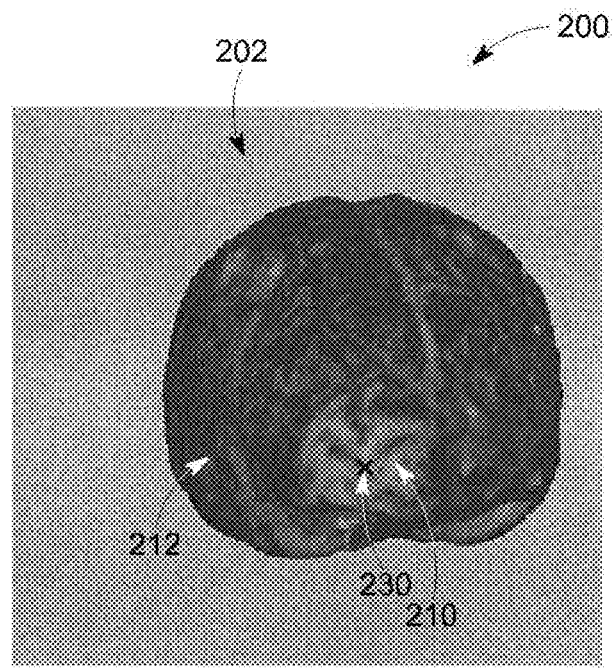
FIG. 3 is an exemplary 3D image that may be generated in accordance with various embodiments.
Figure 4:
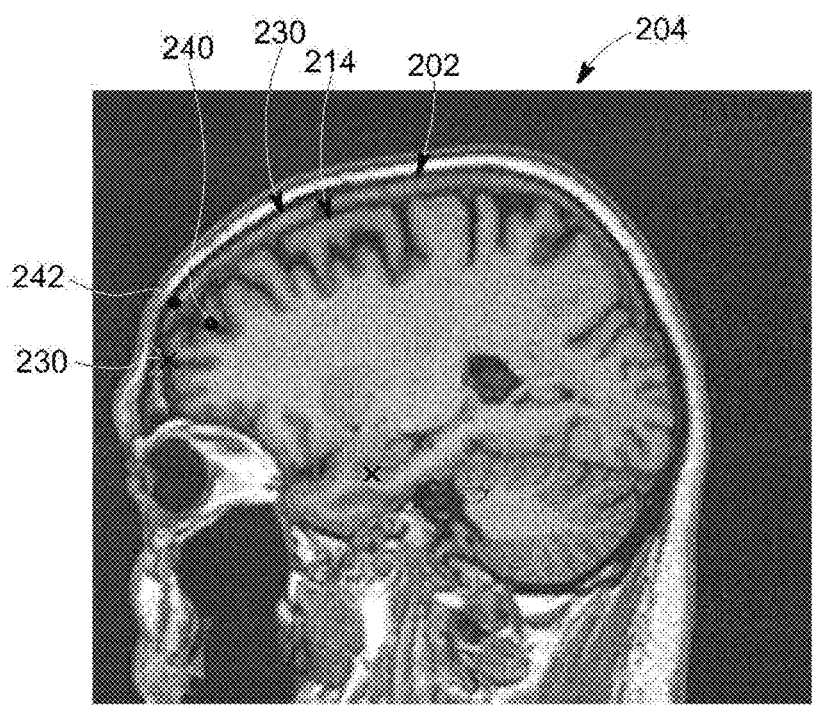
FIG. 4 is an exemplary 2D image that may be generated in accordance with various embodiments.
Figure 5:
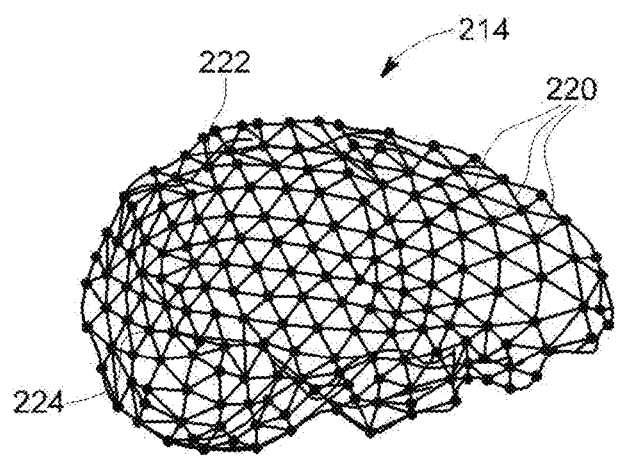
FIG. 5 is sagittal view of a portion of the 3D image that may be generated in accordance with various embodiments.
Figure 6:
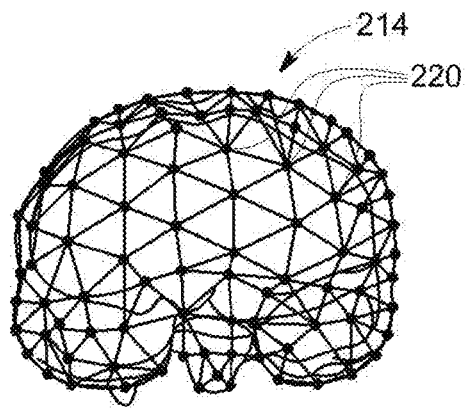
FIG. 6 is coronal view of a portion of the 3D image that may be generated in accordance with various embodiments.
Figure 7:
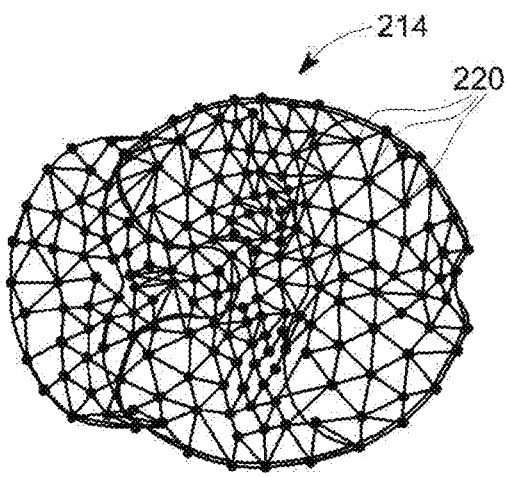
FIG. 7 is an axial view of a portion of the 3D image that may be generated in accordance with various embodiments.

At 106, the segmented information of the brain identified at 104 is utilized to generate and display a 3D image of the brain. For example, FIG. 3 illustrates an exemplary 3D surface rendering 200 of a brain 202 that may be generated and displayed using the information acquired at 104. Additionally, a plurality of two-dimensional images, including the 3D mesh 214 may be displayed concurrently with the 3D image 200. For example, FIG. 4 illustrates an exemplary two-dimensional (2D) image 204 of the brain 202 that may be generated and displayed at 106. It should be realized that although FIG. 4 is a sagittal view of the brain 202, a coronal and/or an axial view of the brain 202 may also be generated and displayed to the operator concurrently with the 3D image 200 of the brain 202. For example, FIG. 5 illustrates a side view of the 3D mesh 214, FIG. 6 illustrates a front view of the 3D mesh 214, and FIG. 7 illustrates a bottom view of the 3D mesh 214.

In operation, the 3D mesh 214 is configured to automatically encapsulate the brain 202 such that the brain 202, or any other selected organ, tissue, or bone, is fully enclosed by the mesh 214. More specifically, the 3D mesh 214 is configured to automatically segment the brain 202 from the surrounding tissue, fluids, and or bones.

In the exemplary embodiment, the mesh 214 is defined by a plurality of vertices or mesh points 220. More specifically, each of the mesh points 220 represents a different coordinate in 3D space. In operation, the mesh 214 may be utilized to enable an operator to visually observe the results of the automatic segmentation performed at 104 to determine whether the mesh 214 fully encapsulates areas of interest or includes areas that are not of interest.

Referring again to FIG. 2, at 108 the 3D mesh 214 may be utilized to navigate the 3D image 202 based on a manual input received from a user indicated on the rendered 3D mesh 214. To manually navigate the 3D image 202, the operator may manually rotate the 3D image in three axes to a user selected orientation, for example, the orientation shown in FIG. 3. More specifically, an operator may position a cursor at a place where the cursor's projection on the 3D brain surface is 230. Three images representing three orthogonal slices including point 230 are displayed. An example of one such slice is shown as the sagittal slice 204 shown in FIG. 4, where the corresponding position of 230 in the sagittal view is at the frontal lobe. It is clear that at this location the frontal part of the brain is cut by the segmentation mesh. Optionally, the three orthogonal slices that are displayed may be displayed concurrently with the movement of the cursor 230. For example, as the operator repositions the cursor 230 on the 3D image 200, the three orthogonal slices are automatically displayed in real time with the movement of the cursor 230.

Thus, the operator may reposition the cursor 230 to different areas of interest on the 3D image 202 and concurrently view the 2D images of the three orthogonal slices represented by the location of the cursor 230. In this manner, the operator may quickly and easily identify areas of interest and concurrently determine whether the mesh 214 is at a desired location by viewing the 2D images 204, which include a visual depiction of the mesh 214 at the location indicated by the cursor 230.

In another embodiment, the operator may reposition the cursor 230 on any one of the 2D images. Again, once the cursor 230 is positioned at a selected point on a 2D image, such as 2D image 204 for example, the 3D image 202 and the remaining 2D images represented by the location of the cursor 230 are automatically updated and displayed.

Thus, various embodiments described herein enable an operator to manually select at least one point on the 3D rendered mesh 214 or on the 3D image 202 and concurrently display three orthogonal slices including 3D mesh points 220 overlaid on the three orthogonal slices based on the selected point corresponding to the 3D location and the user selected orientation. Moreover, the displayed images may be utilized to enable an operator to manually locate areas of interest that are outside the mesh 214 and/or areas of non-interest that are inside the mesh 214.

Figure 8:
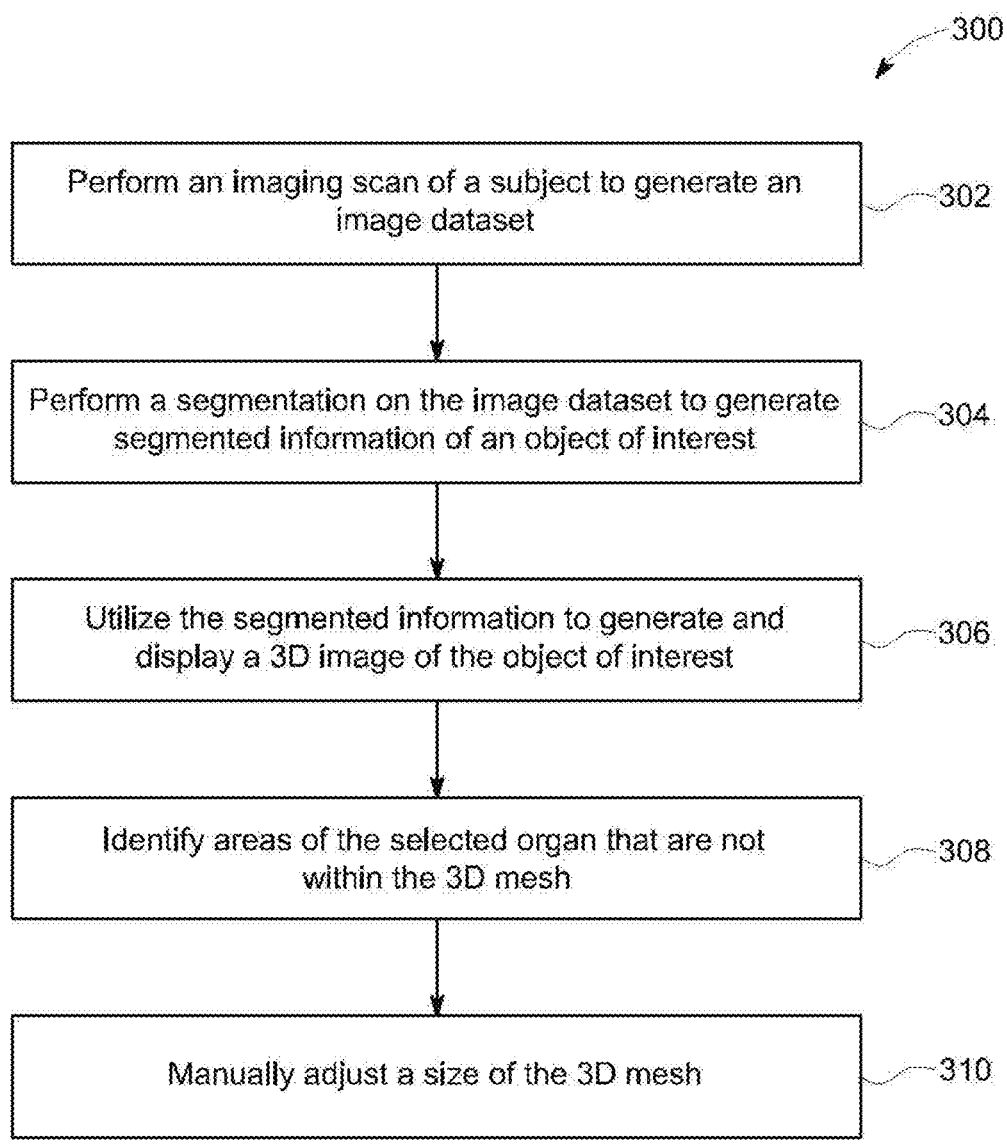
FIG. 8 is a flowchart illustrating an exemplary method of segmenting a 3D image in accordance with various embodiments.

FIG. 8 is a flowchart of an exemplary method 300 for segmenting a 3D image utilizing the imaging system 10 shown in FIG. 1. In the exemplary embodiment, the image segmentation is performed by the 3D image segmentation module 32 based on a manual input received from the operator. However, it should be realized that the various methods of segmenting the 3D image may be implemented using any imaging system and the imaging system 10 shown in FIG. 1 is one embodiment of such an exemplary imaging system. The method 300 may be embodied as a set of instructions that are stored on the computer 20 and/or the segmentation module 30, for example.

At 302, similar to 102, an imaging scan of the subject 12 is performed to generate the raw image dataset 14. As discussed above, in the exemplary embodiment, the image dataset 14 is a 3D volumetric dataset.

At 304, similar to 104, a segmentation algorithm is automatically performed on the 3D image dataset 14 to separate image data related to the brain from image data related to other anatomical structures. In operation, the segmentation algorithm is configured to locate objects of interest, such as the brain, and separate image data of the brain from image data of surrounding objects of lesser or no interest. Accordingly, although various embodiments are described with respect to imaging the brain, other organs of interest may be imaged and segmented as described herein. In the exemplary embodiment, the segmentation algorithm utilizes a surface mesh, such as mesh 214, to automatically compare the density value for each voxel in the image dataset 14 to a predetermined density value, such as using a thresholding process. Additionally, as should be appreciated other suitable segmentation algorithms may be used.

At 306, the segmented information of the brain identified at 304 is utilized to generate and display a 3D image of the brain, for example, the 3D surface rendering 200 of the brain 202 shown in FIG. 3. Additionally, three images representing three different orthogonal slices may be generated. For example, FIG. 4 illustrates a two-dimensional (2D) image 204 of the brain 202 that may be generated at 306. It should again be realized that although FIG. 4 is a sagittal view of the brain 202, a coronal and/or an axial view of the brain 202 may also be generated and displayed to the operator concurrently with the 3D image 200 of the brain 202. For example, FIG. 5 illustrates the side view of the 3D mesh 214, FIG. 6 illustrates the front view of the 3D mesh 202, and FIG. 7 illustrates the top view of the 3D mesh 202.

In operation, the 3D mesh 214 is configured to automatically encapsulate the brain 202 such that the brain 202, or any other selected organ, tissue, or bone, is fully enclosed by the mesh 214. More specifically, the 3D mesh 214 is configured to automatically segment the brain 202 from the surrounding tissue, fluids, and or bones.

Referring again to FIGS. 5-7, the mesh 214 is defined by the plurality of mesh points 220 wherein each of the mesh points 220 represents a different coordinate in 3D space. In the exemplary embodiment, at least some of the mesh points may be assigned a color that represents an intensity value, or brightness, of the voxel at the respective 3D coordinate represented by the point. The color may be represented as gray scale values based on the intensity value. Optionally, the color may be represented as different colors, e.g., red, blue, green, etc. For example, a point 222 may be represented using a light gray color indicating the intensity value at this location is relatively low. Moreover, a point 224 may be represented as a black color indicating that the intensity value at this location is relatively high. The color mesh points 220 enable an operator to visually determine whether the mesh 214 has fully encapsulated the object of interest, e.g., the brain 202. In operation, the colored mesh 214 may be utilized to enable an operator to visually observe the results of the automatic segmentation performed at 104 to determine whether the mesh 214 fully encapsulates areas of interest or includes areas that are not of interest.

Referring again to FIG. 4, in the exemplary embodiment, the mesh 214 does not fully encapsulate the brain 202 as desired. As a result, the mesh 214 is located such that at least a portion of the brain, indicated by a point 240 lies, at least partially inside the brain 202. For example, referring again to FIG. 3, the lightly shaded regions, such as a region 210, represent areas outside the brain 202. Additionally, the dark shaded regions, such as a region 212, represent the brain 202, itself.

Referring again to FIG. 8, at 308 the 3D mesh 214 may be utilized to identify areas of the selected organ that are not within the 3D mesh 214. To identify areas that are not within the mesh 214, the operator may manually rotate the 3D image in three axes to a user selected orientation, for example, the orientation shown in FIG. 3. More specifically, to identify areas of interest, an operator may position the cursor 230 on the 3D image 200. Once the cursor 230 is positioned at the desired point on the 3D image, the operator may manually click the selected point, using a mouse for example. Once a point is selected, three orthogonal slices including the 3D mesh points 220 overlaid on the three orthogonal slices are displayed. An example of one such slice is shown as the sagittal image 204 shown in FIG. 4. Optionally, the three orthogonal slices are displayed may be displayed concurrently with the movement of the cursor 230. For example, as the operator repositions the cursor 230 on the 3D image 200, the three orthogonal slices are automatically displayed in real time with the movement of the cursor 230.

Thus, the operator may reposition the cursor 230 to different areas of interest on the 3D image 200 and concurrently view the 2D images of the three orthogonal slices represented by the location of the cursor 230. In this manner, the operator may quickly and easily identify areas of interest and concurrently determine whether the mesh 214 is at a desired location by viewing the 2D images 204 which include a visual depiction of the mesh 214 at the location indicated by the cursor 230.

In another embodiment, the operator may reposition the cursor 230 on any one of the 2D images. Again, once the cursor 230 is positioned at a selected point on a 2D image 204, the 3D image 200 and the remaining 2D images represented by the location of the cursor 230 are automatically updated and displayed.

Referring again to FIG. 8, at 310, a size or location of the mesh 214 may be manually adjusted based on the determination made at 308. More specifically, the mesh 214 may be adjusted to remove undesired areas that are currently encapsulated by mesh 214 or to add desired areas that are currently not encapsulated by the mesh 214. For example, referring again to FIG. 4, the mesh 214 may be adjusted to such that the lightly shaded region 210, which represent an area outside of the brain 202 is removed from the segmentation information.

Figure 9:
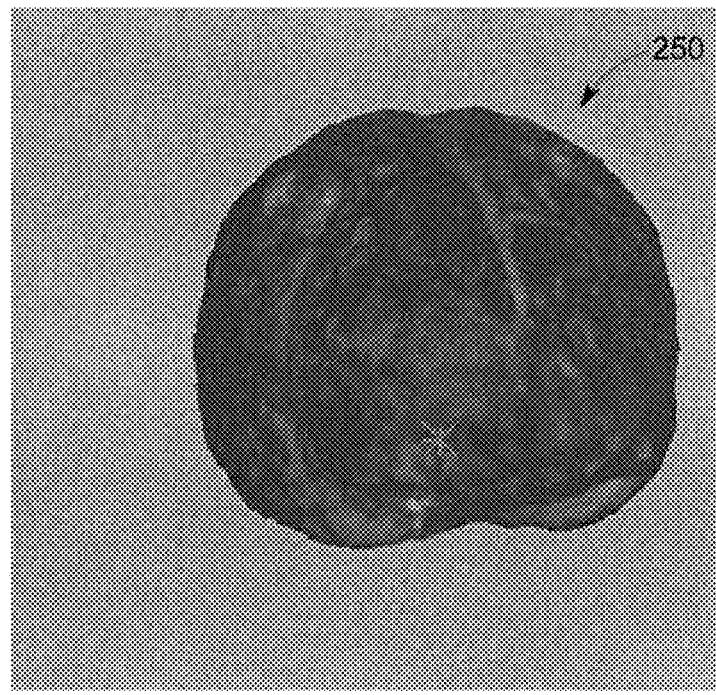
FIG. 9 is another exemplary 3D image that may be generated in accordance with various embodiments.
Figure 10:
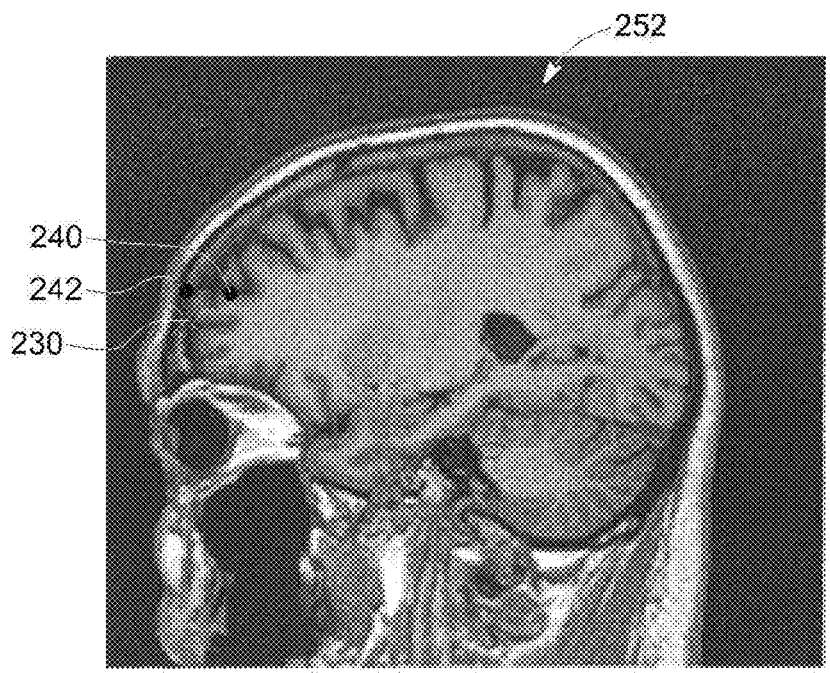
FIG. 10 is another exemplary 2D image that may be generated in accordance with various embodiments.

To resize the mesh 214, and thus remove undesired areas or add desired areas, the operator may position the cursor 230 at any point on any one of the 2D images such as point 242 shown on the image shown in FIG. 4. For example, in one embodiment, the operator may manually position the cursor at the point 230 as shown in FIG. 3. The corresponding position of 230 in the sagittal view is shown in FIG. 4. It is clear some brain areas near the point 230 are cut by the segmentation mess. The operator may manually click a point 242 at or near point 230 where you want segmentation mesh to reach. The mesh 214 is automatically resized in three dimensions using point 242 as reference. Moreover, a revised 3D image and a set of revised 2D images are automatically displayed. For example, FIG. 9 represents a revised 3D image 250 showing the results of the 3D segmentation based on the resized mesh 214. Moreover, FIG. 10 is a 2D image 252 generated and displayed based on the resized mesh 214, which includes the mesh 214 located at the revised position indicated by the cursor position 230. Again, it should be realized that although only the sagittal view of the resize mesh 214 is shown, that in the exemplary embodiment, a coronal view or a axial view of the revised mesh 214 may be displayed concurrently with the sagittal view shown as image 252.

In the exemplary embodiment, the mesh 214 may be resized at 310 using an iterative geometry-based image manipulation method (GIMMIE). In operation, GIMMIE enables an operator to view a 3D image of the organ of interest with the segmentation mesh 214 overlayed on the organ. The operator may then manually manipulate the mesh 214 while visualizing the image and the mesh 214. GIMMIE enables the operator to select a "pull point" such as the point 242. GIMMIE then automatically resizes the mesh 214 based on the position of the reference point 242 selected by the operator. In another embodiment, the operator may select a pull point to resize the mesh on any one of the 2D images. GIMMIE operates independent of image properties. After the mesh manipulations are completed, the desired VOI is extracted and used to generate a revised 3D image of the organ of interest.

Figure 11:
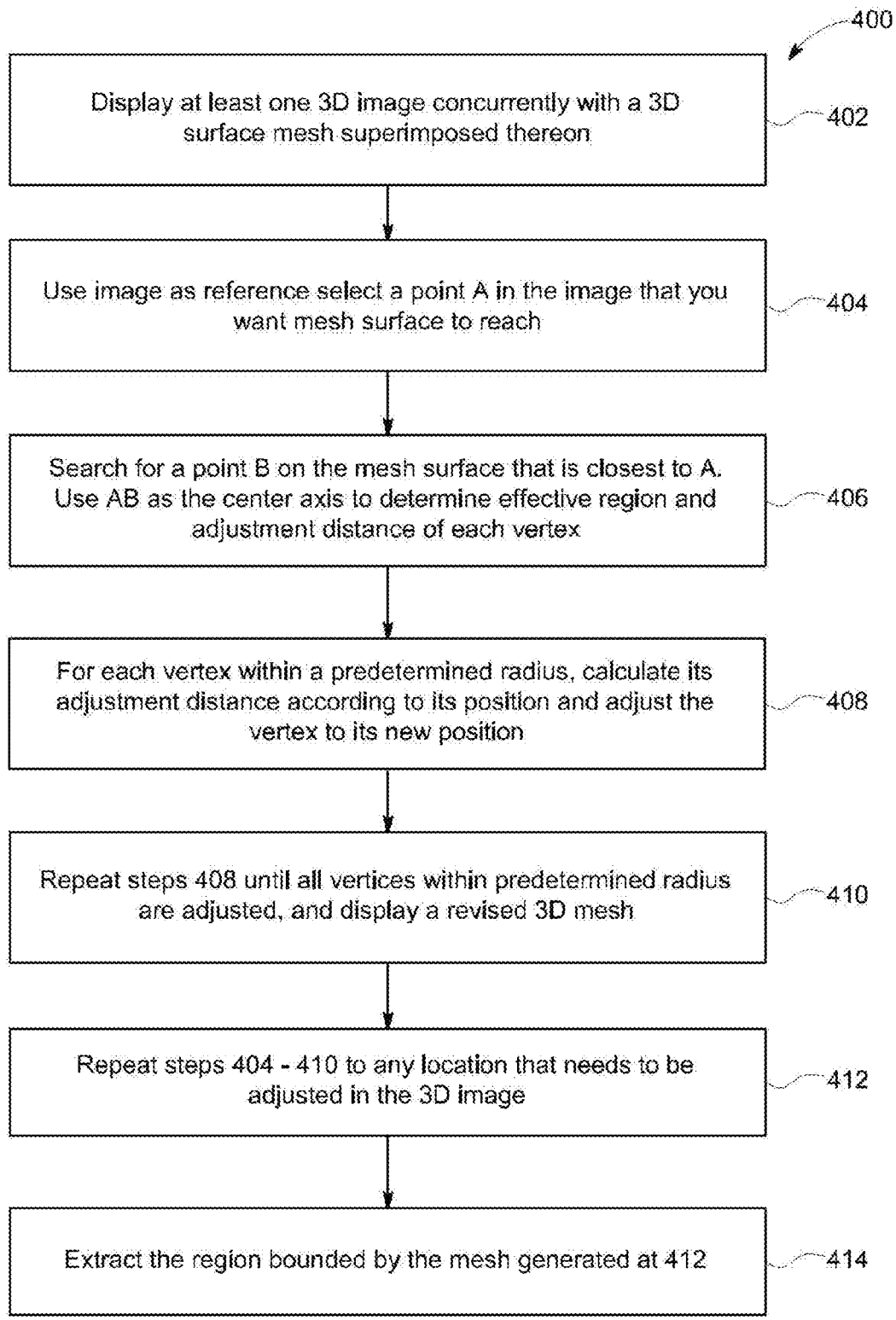
FIG. 11 is a flowchart illustrating an exemplary method of editing a 3D surface mesh in accordance with various embodiments.
Figure 12:
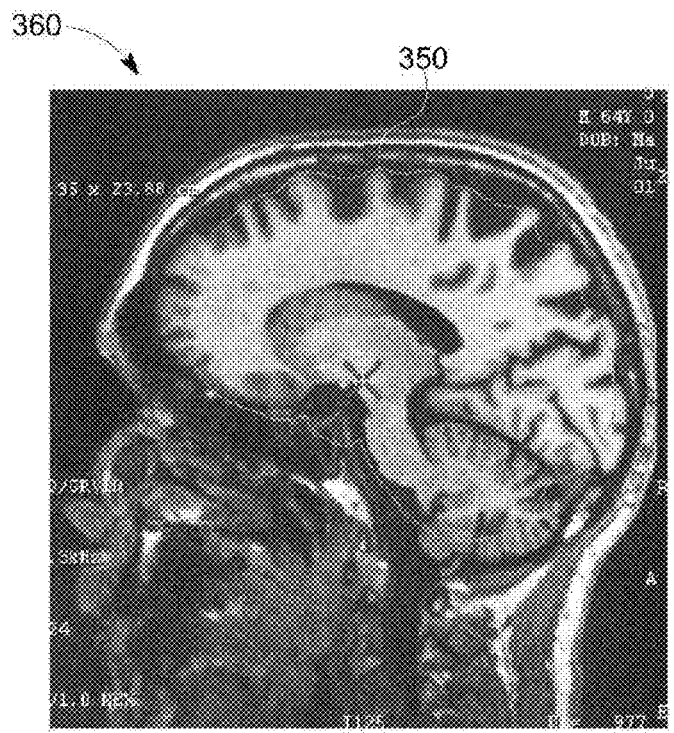
FIG. 12 is another exemplary 2D image that may be generated in accordance with various embodiments.
Figure 13:
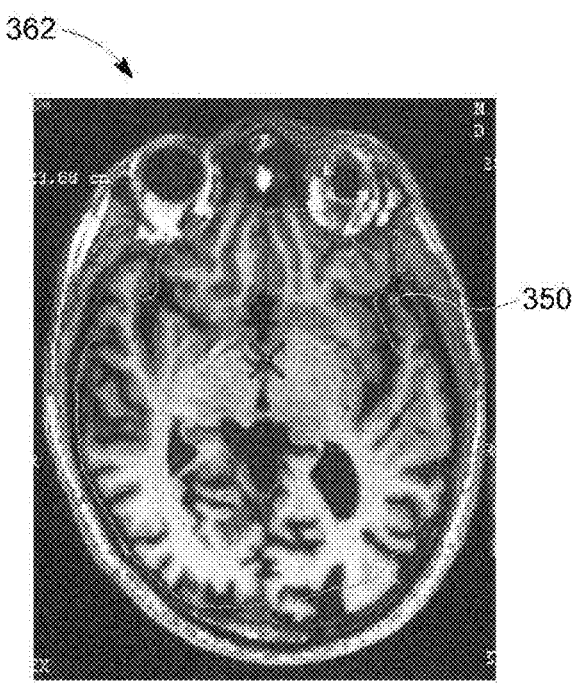
FIG. 13 is another exemplary 2D image that may be generated in accordance with various embodiments.
Figure 14:
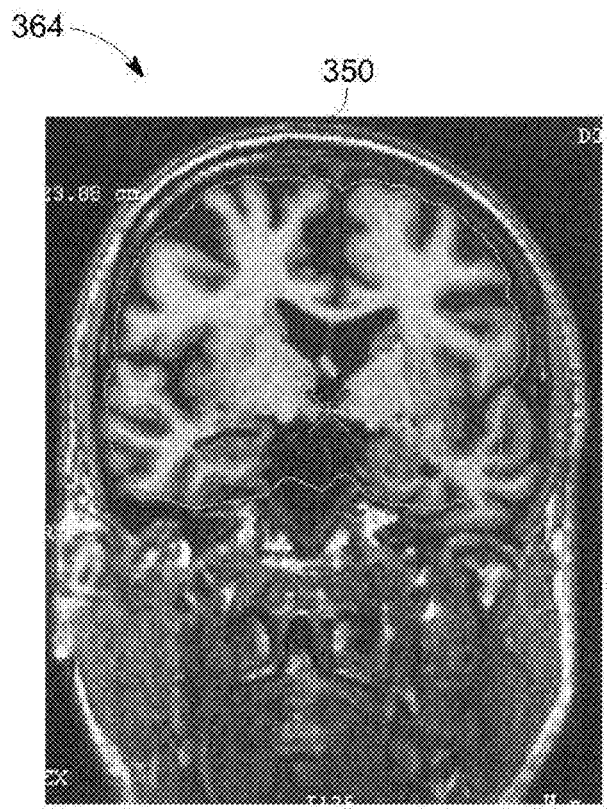
FIG. 14 is another exemplary 2D image that may be generated in accordance with various embodiments.

In the exemplary embodiment, modifying the size or location of an exemplary mesh, such as mesh 214, using GIMIMIE, may be provided using a method 400 shown in FIG. 11. As shown in FIG. 11, at 402 at least one, and preferably a plurality of views of the 3D image dataset are displayed concurrently with an initial 3D surface mesh 350 overlayed on each of the views. For example, FIG. 12 illustrates an exemplary sagittal image 360 having a mesh 350 overlayed thereon. FIG. 13 illustrates an exemplary axial image 362 having the mesh 350 overlayed thereon. FIG. 14 illustrates an exemplary coronal image 364, each having the mesh 350 overlayed thereon.

Figure 15:
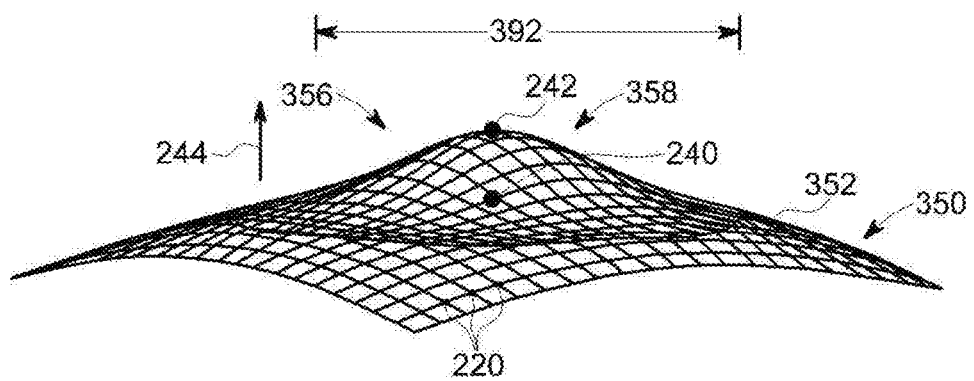
FIG. 15 is an illustration of an exemplary mesh that may be generated in accordance with various embodiments.

Referring to FIGS. 11 and 15, at 404, a pull point on the initial 3D mesh 350, such as pull point 242, is selected by the operator as discussed above. For simplicity, the pull point 242 is also referred to herein as the "end point" 242, which represents the location in which the operator desires to reposition a portion of the mesh 350. At 406, a point on the mesh surface that is closest to the pull point 242 is identified. In the exemplary embodiment, the mesh point 240 shown in FIG. 15 is determined to be closest to the pull point 242.

At 408, the adjusting distance of the mesh point 240 is determined by calculating a difference between the coordinates of the pull point 242 and the coordinates of the mesh point 240. The adjusting direction is also determined by the points 242 and 240. The vertex at point 240 is then moved to the pull point 242. The effective radius of the update area on the mesh surface can be preselected or calculated by analyzing the shape of the image surface. The update area on the image surface is centered at mesh point 240. At 410, the steps 404 to 408 are repeated until all the vertices within the update area are calculated and adjusted to the revised position indicated by the pull point 242 while concurrently displaying a revised 3D image 200 and revised 3D mesh shown in FIGS. 12-14. More specifically, as each pull point 242 is selected by the operator, the 3D image 200 and the 2D images showing the revised location of the mesh 350 are automatically updated in real time to reflect the revised location of the mesh 350. Referring again to FIG. 11, at 412, steps 404-410 are repeated for each portion of the mesh 350 that the operator desires to reposition. It should be realized that each portion of the mesh 350 may be repositioned by manually selecting a pull point at the point on the image that the operator desires to move the mesh. At 414, a region encompassed by the repositioned mesh is extracted as discussed in more detail below.

In the exemplary embodiment, adjusting the size of the initial mesh 350 is implemented by calculating a distance between the pull point 242 and the selected point 240 that represents the nearest vertex to the point 242. For each vertex in the area defined between the pull point 242 and the point 240, a vertex shift distance and shift direction are calculated. The calculated shift distance and shift direction are then utilized to update the visual location of the initial mesh 350 in real time.

For example, FIG. 15 illustrates an initial position of the mesh 350. The mesh 350 is defined by the plurality of vertices or mesh points 220. The plurality of mesh points 220 therefore define a surface 352 of the initial mesh 350 at the initial position. The surface 352 represents the location of the mesh 350 indicated by the mesh points 240. In the exemplary embodiment, the mesh 350 may be defined by a plurality of polygons such as triangles or squares wherein each vertex has multiple neighboring vertices. Moreover, point 242 represents the point in 3D space to which the operator desires to move a portion of the mesh 350. Accordingly, in operation, the operator clicks on the pull point 242. The segmentation algorithm automatically identifies a local area 356 around the mesh point 240 and transitions the local area 352 to the revised area 356. In the exemplary embodiment, the transition between the area 352 and the area 356 is substantially smooth and the edge of the updated local surface are 356 is smoothly transitioned to the original mesh surface 352.

Figure 16:
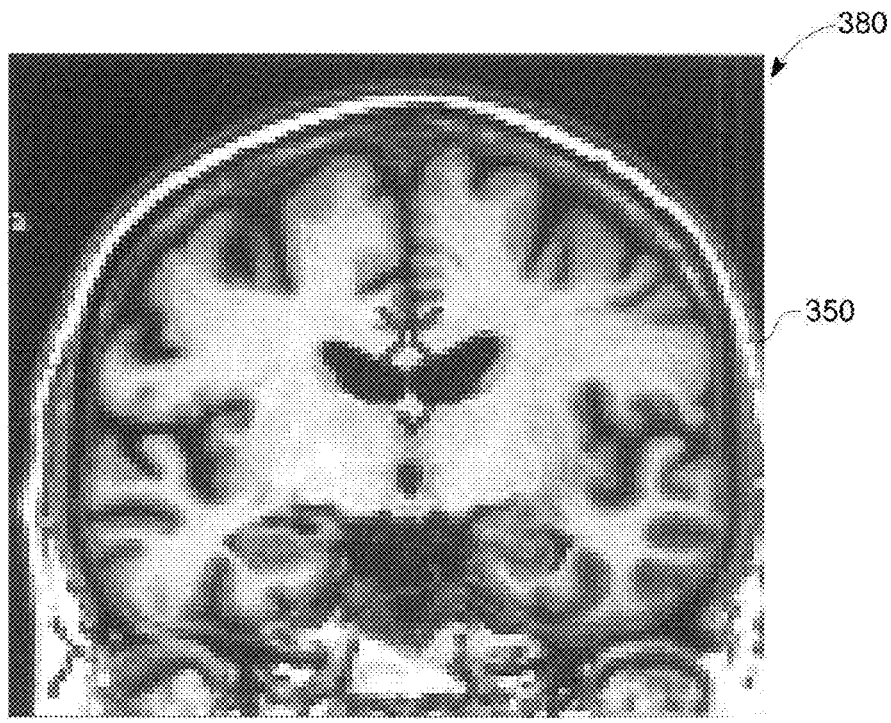
FIG. 16 is another exemplary 3D image that may be generated in accordance with various embodiments.
Figure 17:
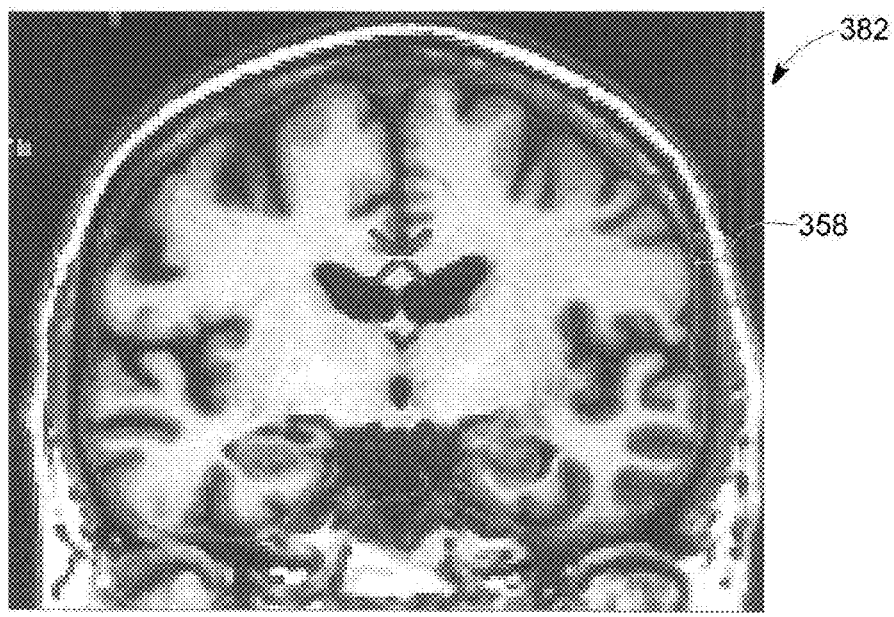
FIG. 17 is another exemplary 3D image that may be generated in accordance with various embodiments.

In the exemplary embodiment, the initial mesh 350 may have any shape. In the embodiment described herein, a surface 352 of the mesh 350 is shaped to conform to the brain 202. However, it should be realized that the mesh surface 352 may have any shape to conform to an organ having any shape. Accordingly, in operation, for each vertex in the mesh, its neighbor vertices are calculated. The initial mesh 350 is then positioned in the head image 200 for auto-deformation. The auto-deformation method then drives each vertex on the brain mesh 214 moving towards the brain surface to generate an image that includes the final mesh 358. For example, FIG. 16 illustrates an exemplary image 380 showing the location of the initial mesh 350 at the mesh point 240. Additionally, FIG. 17 illustrates an exemplary image 382 showing the location of the final mesh 358 at the pull point 242 after being automatically adjusted as described herein. In operation, shifting or moving the initial mesh 350 from the point 240 to the point 242 includes editing hundreds or thousands of vertices on the mesh surface 352 three-dimensionally using only a single click. In one embodiment, editing may include editing more or less than hundreds or thousands of vertices.

More specifically, referring again to FIG. 15, in operation the operator selects the pull point 242. The coordinates of the pull point 242 are identified, using for example, the segmentation module 32. At 408, an adjusting distance between the pull point 242 and the nearest mesh point 240 is determined by calculating a difference between the coordinates of the pull point 242 and the coordinates of the point 240. The vertices of the initial mesh 350 are adjusted while concurrently displaying a revised 3D image 200 and revised images shown in FIGS. 12-14.

More specifically, in operation, the operator selects the pull point 242. The module 32 then searches for a vertex on the mesh surface that is closest to the pull point 242, such as for example, a vertex 240. A radial size of an update area 392 is then determined by the curvature of the surface 352 or uses a predetermined value. In one embodiment, if the size of the update area 392 is relatively larger, a radial size of the update area 392 is selected be between, or example, approximately 80 and 100 mm. Optionally, if the radial size of the update area 392 is relatively small, the radial size of the update area 392 may be selected between, for example, approximately 40 and 60 mm. It should be realized that update area 392 may have different sizes than the exemplary sizes described herein. The segmentation module 32 calculates the direction of the surface updating based on the movement of the point 240 to the point 242, using for example, a direction vector that indicates the radial movement and magnitude of the changes.

For example, the updating direction 244 is parallel to a line extending between points 240 and 242. In the exemplary embodiment, the vertices in the updating area 392 are parallel shifted. To generate a smooth transition between the surface 352 and the surface 358, the shift distance of each vertex is calculated consistently with a damping factor σ that is determined by the update radius. Thus, 3D updating is simplified as a 1D calculation.

In the exemplary embodiment, the shift function utilized to parallel shift the vertices may be calculated in accordance with:

$$s(v_i) = l \cdot \exp\left(-\frac{[d(v_i)]^2}{2\sigma^2}\right) \quad \text{Equation 1}$$

where: l is the distance between the end point 242 and the closest vertex;

$d(v_i)$ is the distance between the vertex $v_i$ and to a line connecting point 240 and point 242; and σ is the damping factor utilized to control the damping of the shift distance for each vertex in the updating area 392.

In the exemplary embodiment, to enable the final mesh 358 to smoothly merge with the initial mesh 350 in the boundary of the updating area 392, σ is set smaller than R/3. Where R is the radial size of the updating area. The position of the final mesh 358 is then calculated in accordance with:

$$\vec{p}'(v_i) = \vec{p}_0(v_i) + s(v_i) \cdot \vec{n} \quad \text{Equation 2}$$

where $\vec{n}$ is the direction from point 240 to point 242; and $\vec{p}_0$ and $\vec{p}'$ are the original and updated vertex positions. The processing steps of 3D mesh editing are shown in the FIG. 11.

Referring again to FIG. 11, at 412, steps 404-410 are repeated until the mesh 214 is at the location desired by the operator, e.g. until the operator is satisfied with the 3D region defined by the 3D surface mesh 214. At 414, the region bounded by the 3D mesh may be extracted as a revised 3D image. More specifically, the region encapsulated by the 3D mesh may be extracted to form a separate 3D image that includes only the information selected by the operator to be within the 3D mesh.

Various embodiments described above provide an editing tool that multiple image points to be updated in a single operation. The updated image surface is smooth and natural. The various embodiments enable an operator to manually select at least one point on the 3D rendered mesh 214 or on the 3D image 200 and concurrently display three orthogonal slices including 3D mesh points 220 overlaid on the three orthogonal slices based on the selected point corresponding to the 3D location and the user selected orientation. Moreover, the displayed images may be utilized to enable an operator to manually resize the mesh to either add areas of interest or delete areas that are not of interest. The various embodiments are implemented in real time and may be used different applications in different modalities.

Figure 18:
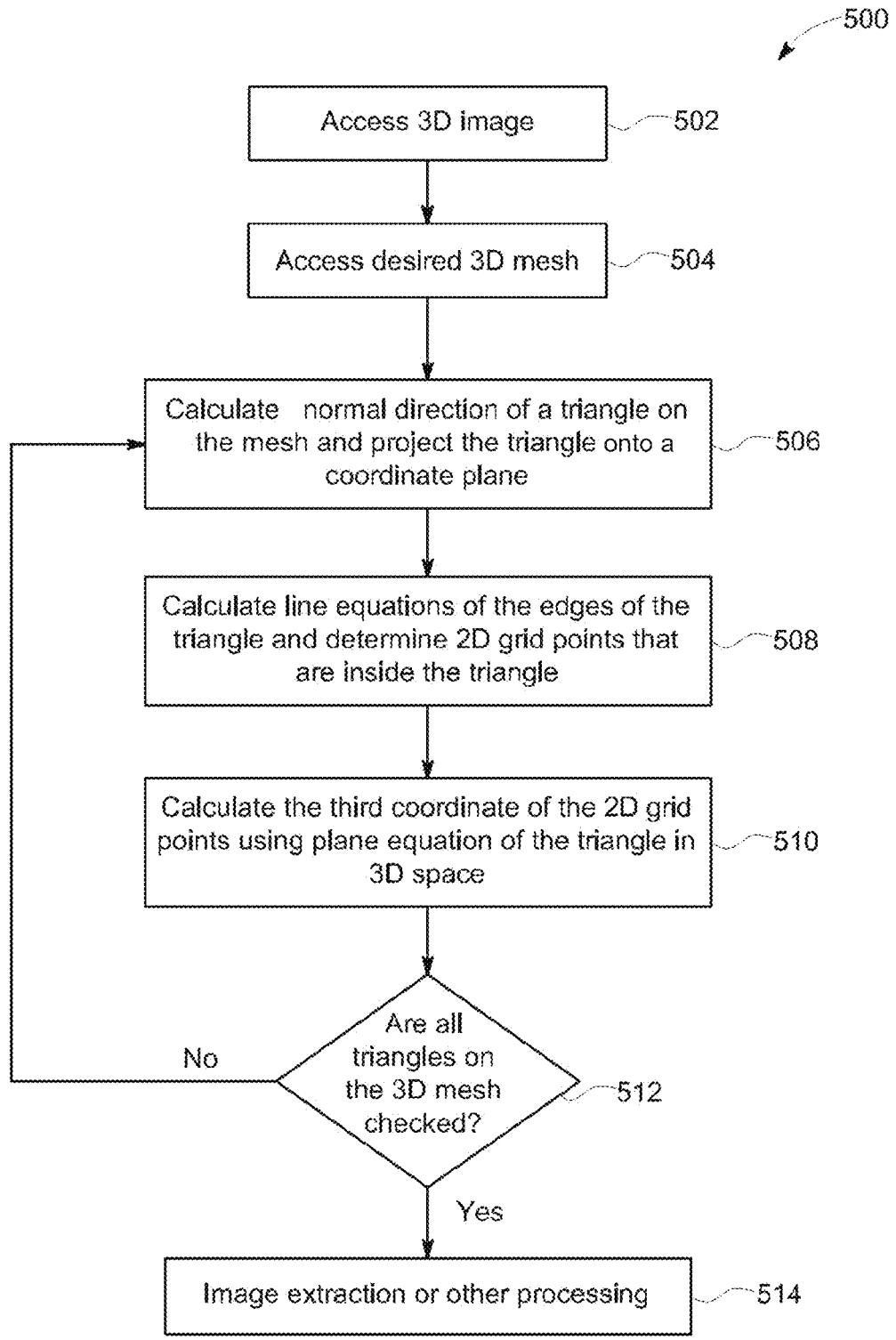
FIG. 18 is a flowchart illustrating an exemplary method of extracting a 3D image from a 3D image dataset in accordance with various embodiments.

FIG. 18 is a flowchart illustrating an exemplary method 500 of extracting a 3D image from a 3D image dataset. In the exemplary embodiment, the object of interest is the brain 202. However, it should be realized that the method 400 may be utilized to extract any object of interest within a 3D image dataset. In the exemplary embodiment, the image extraction is performed by the 3D image extraction module 34 (shown in FIG. 1) based on a manual input received from the operator. However, it should be realized that the various methods of extracting the 3D image may be implemented using any imaging system and the imaging system 10 shown in FIG. 1 is one embodiment of such an exemplary imaging system. The method 500 may be embodied as a set of instructions that are stored on the computer 20 and/or the segmentation module 30, for example.

At 502, an imaging scan of the subject 12 is performed, similar to 102 and 302, to generate the raw image dataset 14. As discussed above, in the exemplary embodiment, the image dataset 14 is a 3D volumetric dataset.

At 504, a desired 3D mesh is placed on a region of interest of the 3D image. In operation, the desired mesh is configured to locate objects of interest, such as the brain, and segment separate image data of the brain from image data of surrounding objects of lesser or no interest. Accordingly, although various embodiments are described with respect to imaging the brain, other organs of interest may be imaged and segmented as described herein. In the exemplary embodiment, the surface automatically compares the density value for each voxel in the image dataset 14 to a predetermined density value, such as using a thresholding process. The desired mesh may be defined by a plurality of polygons such as triangles or squares wherein each vertex has multiple neighboring vertices. In the exemplary embodiment, the desired mesh is defined by a plurality of triangles.

Figure 19:
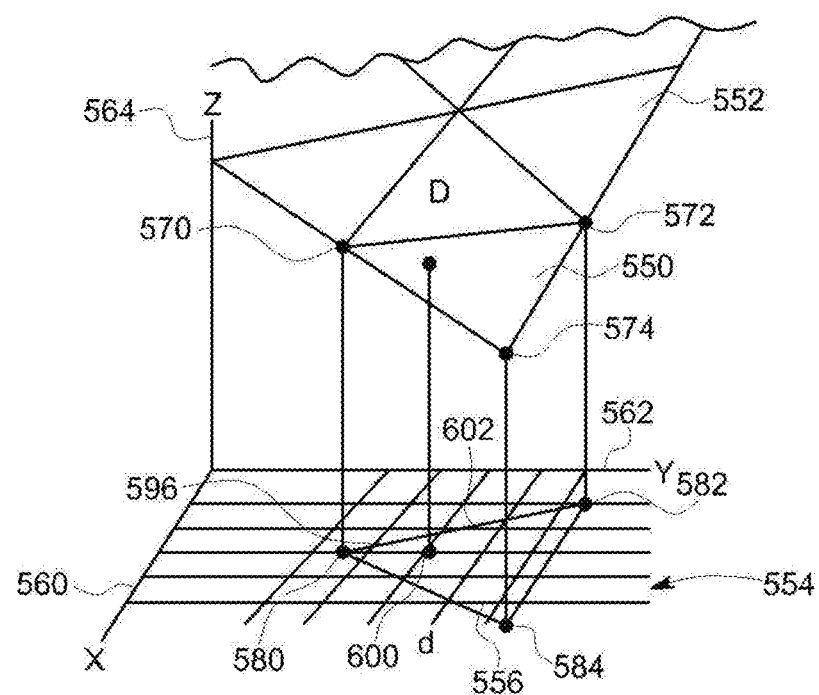
FIG. 19 is an exemplary model illustrating the method shown in FIG. 18.

At 506, a normal direction of a triangle forming the desired mesh is calculated and projected on a coordinate plane. FIG. 19 illustrates an exemplary triangle 550 that forms part of a desired mesh 552. As shown in FIG. 19, the triangle 550 is projected onto an exemplary surface or projection plane 554 in accordance with various embodiments. The projected triangle is depicted as triangle 556. The surface plane 554 is defined by an x-axis 560 and a y-axis 562. Moreover, the projection space is defined by the x-axis 560, the y-axis 562, and a z-axis 564.

Accordingly, the coordinates of the triangle 550 are defined as (x1, y1, z1), (x2, y2, z2), and (x3, y3, z3) wherein (x1, y1, z1) represents a first point or corner 570 of the triangle 550, (x2, y2, z2) represents a second point or corner 572 of the triangle 550, and (x3, y3, z3) represents a third point or corner 574 of the triangle 550. Moreover, the coordinates of the projected triangle 556 are defined by (x1, y1) which represents a first point or corner 580 of the triangle 556, (x2, y2) which represents a second point or corner 582 of the triangle 556, and (x3, y3) which represents a third point or corner 584 of the triangle 556.

Step 506 also includes identifying grid points that are located inside the projected triangle 556. To identify the grid points located inside the projected triangle 556, and referring again to FIG. 19, a line 596 is formed to divide the (x, y) plane into two parts defined between the first point 580 and the second point 582. In the exemplar embodiment, the line 596 (y) is calculated in accordance with:

$$y = \frac{y2-y1}{x2-x1}x + y1 - \frac{y2-y1}{x2-x1}x1 \qquad \text{Equation 3}$$

In the exemplary embodiment, the x and y search areas of Equation 3 are limited to a rectangle that is described as:

$$\min(x1, x2, x3) \le x \le \max(x1, x2, x3) \qquad \text{Equation 4}$$
$$\min(y1, y2, y3) \le y \le \max(y1, y2, y3)$$

To determine whether a grid point, such as a grid point 600, is located inside the projected triangle 556, the position of the line y to a position of the third point 584 (x3, y3) of the projected triangle is calculated at 510. More specifically, the line y described in Equation 3 divides the (x, y) projection plane 554 into two parts. If a selected grid point is not on the same side as the third point 602 (x3, y3) or on the line 596, the selected grid point is determined to be outside the projected triangle 586. In the exemplary embodiment, the line passing through the third point 602 (x3, y3) location may be determined using Equation 3 and the coordinates of the third point 585 (x3, y3). Similarly, the lines passing through the first and second points 580 and 582 (x2, y2) and (x3, y3), may be calculated in the same manner as the line passing through the third points 584 to identify grid points in the rectangular search space, but are not inside the projected triangle 556. The grid points remaining in the rectangle search area are then selected to be interpolated as discussed in more detail below.

For each grid point that is bounded by the triangle 556, the third coordinate z can be calculated from Equation 5. At 512, steps 506-510 are repeated for each triangular portion forming the desired mesh 552 to generate an enclosed 3D masking surface:

$$\begin{vmatrix} x-x1 & y-y1 & z-z1 \\ x2-x1 & y2-y1 & z2-z1 \\ x3-x1 & y3-y1 & z3-z1 \end{vmatrix} = 0 \qquad \text{Equation 5}$$

At 514, the volume encapsulated by the final 3D surface mesh is extracted. In the exemplary embodiment, the maximum and minimum coordinates of the final 3D surface mesh in three directions are calculated to identify the 3D volume selected for extraction in accordance with Equation 5. Accordingly, each point in the desired mesh 552 is checked in three directions to determine the whether the point is inside the enclosed mesh. If the selected point is inside the mesh, the data of the point is extracted to generate the 3D image.

Figure 20:
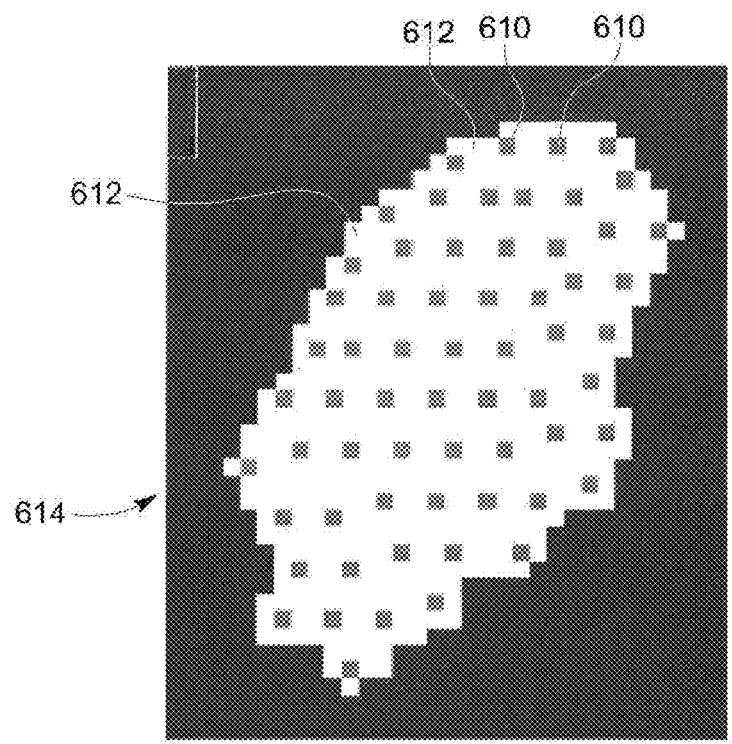
FIG. 20 illustrates an exemplary surface mesh that may be generated in accordance with various embodiments.
Figure 21:
FIG. 21 is an image of an organ that may be generated using the surface mesh shown in FIG. 20.
Figure 22:
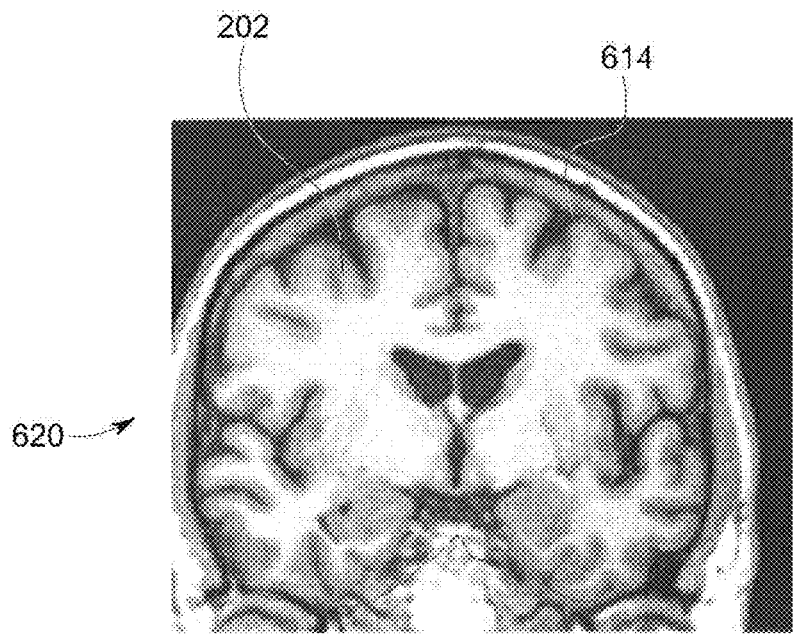
FIG. 22 is 2D image of a portion of an organ and an exemplary surface mesh that may be generated in accordance with various embodiments.
Figure 23:
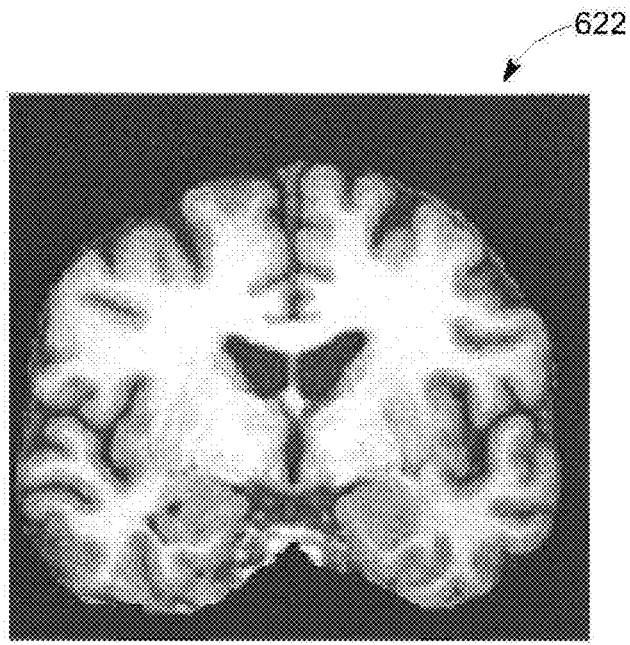
FIG. 23 is an image of a 2D slice that may be extracted using the surface mesh shown in FIG. 22.

For example, FIG. 20 is an image of the initial 3D mesh 552 and FIG. 21 a 2D image of the brain encapsulated by the initial mesh 552. As shown in FIG. 20, the black squares 610 are the vertices on the mesh surface 552 and the white squares 612 are the interpolated points derived as discussed above. Together, the white and the black squares 610 and 612 create a complete enclosed surface mesh 614. Moreover, FIG. 22 is a coronal view 620 of the brain 202 including the final surface mesh 614 and FIG. 23 is a 2D slice 622 of the brain 202 that may be generated using the final surface mesh 614.

A technical effect of various embodiments enables automatic searching for the interpolation points in 3D grid space and creating a complete set of 3D interpolation points. The original mesh vertices and the searched interpolation points form a complete 3D surface that encloses an image volume to be extracted. More specifically, various embodiments, project each mesh triangle onto a 2D plane to search for 3D interpolation points that are enclosed in the triangle.

Figure 24:
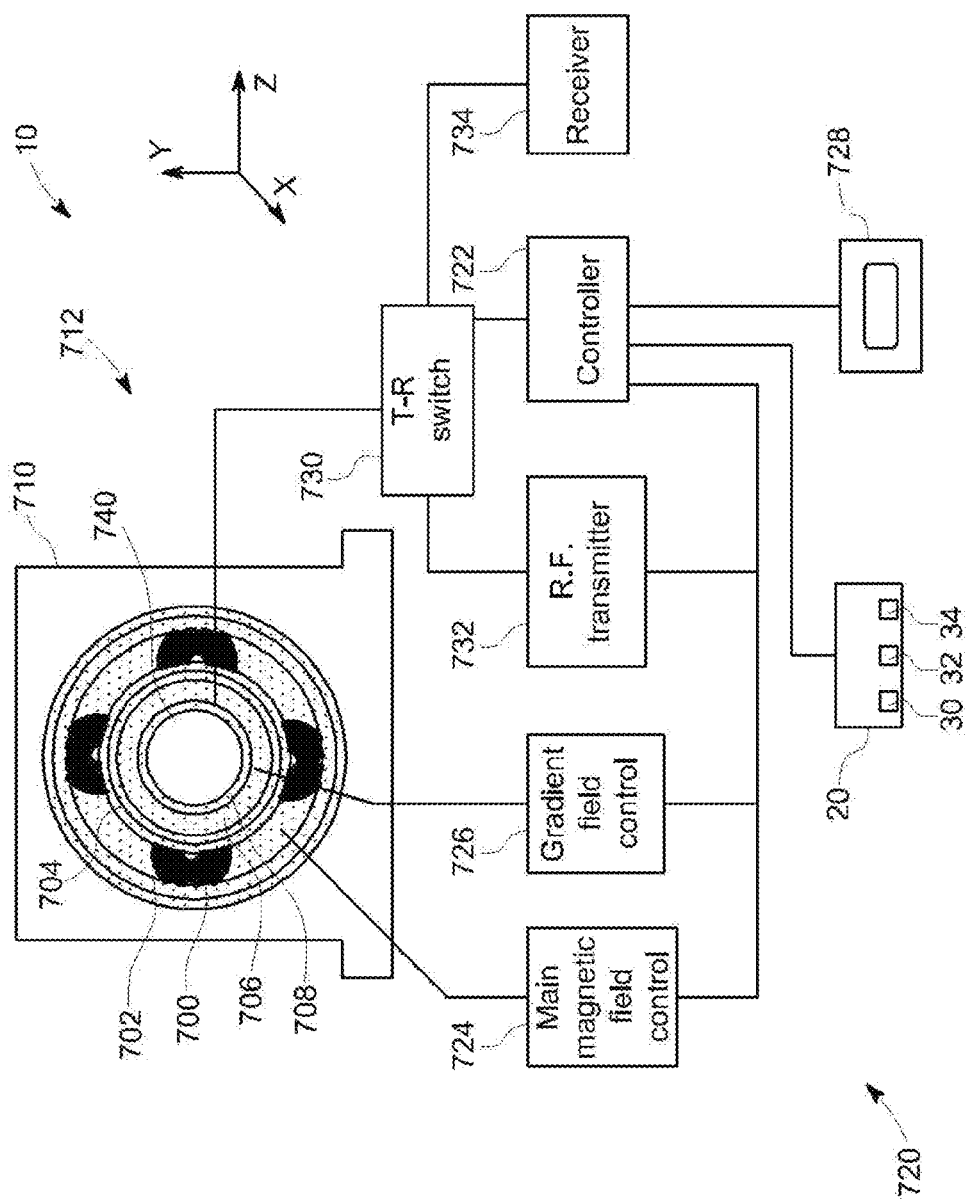
FIG. 24 is an exemplary imaging system formed in accordance with various embodiments.

FIG. 24 is a schematic block diagram of the imaging system 10 shown in FIG. 1. In the exemplary embodiment, the imaging system 10 is an MM system and also includes a superconducting magnet 700 formed from magnetic coils supported on a magnet coil support structure. However, in other embodiments, different types of magnets may be used, such as permanent magnets or electromagnets. A vessel 702 (also referred to as a cryostat) surrounds the superconducting magnet 700 and is filled with liquid helium to cool the coils of the superconducting magnet 700. A thermal insulation 704 is provided surrounding the outer surface of the vessel 702 and the inner surface of the superconducting magnet 700. A plurality of magnetic gradient coils 706 are provided within the superconducting magnet 700 and an RF transmit coil 708 is provided within the plurality of magnetic gradient coils 706. In some embodiments the RF transmit coil 708 may be replaced with a transmit and receive coil as described in more detail herein. The components described above are located within a gantry 710 and generally form an imaging portion 712. It should be noted that although the superconducting magnet 700 is a cylindrical shaped, other shapes of magnets can be used.

A processing portion 720 generally includes a controller 722, a main magnetic field control 724, a gradient field control 726, the computer 20, a display device 728, a transmit-receive (T-R) switch 730, an RF transmitter 732 and a receiver 734. In the exemplary embodiment, the computer 20 includes the 3D image navigation module 30 that enables an operator to navigate the 3D image based on a manual input received from an operator. The computer also 20 includes the segmentation module 32 to segment the 3D image dataset 14 to generate a segmented 3D image 22. The computer 20 further includes the object extraction module 34 to extract a 3D image of an exemplary object or organ (not shown) from the 3D image dataset 14.

In operation, a body of an object, such as a patient (not shown), is placed in a bore 740 on a suitable support, for example, a motorized table (not shown) or other patient table. The superconducting magnet 700 produces a uniform and static main magnetic field $B_o$ across the bore 740. The strength of the electromagnetic field in the bore 740 and correspondingly in the patient, is controlled by the controller 722 via the main magnetic field control 724, which also controls a supply of energizing current to the superconducting magnet 700.

The magnetic gradient coils 706, which include one or more gradient coil elements, are provided so that a magnetic gradient can be imposed on the magnetic field $B_o$ in the bore 740 within the superconducting magnet 700 in any one or more of three orthogonal directions x, y, and z. The magnetic gradient coils 706 are energized by the gradient field control 726 and are also controlled by the controller 722.

The RF transmit coil 708, which may include a plurality of coils (e.g., resonant surface coils), is arranged to transmit magnetic pulses and/or optionally simultaneously detect MR signals from the patient if receive coil elements are also provided, such as a surface coil (not shown) configured as an RF receive coil. The RF transmit coil 706 and the receive surface coil are selectably interconnected to one of the RF transmitter 732 or the receiver 734, respectively, by the T-R switch 730. The RF transmitter 732 and T-R switch 730 are controlled by the controller 722 such that RF field pulses or signals are generated by the RF transmitter 732 and selectively applied to the patient for excitation of magnetic resonance in the patient.

Following application of the RF pulses, the T-R switch 730 is again actuated to decouple the RF transmit coil 708 from the RF transmitter 732. The detected MR signals are in turn communicated to the controller 722. The controller 722 may include a processor (e.g., the Diffusion Spectrum Imaging (DSI) module 30. The processed signals representative of the image are also transmitted to the display device 728 to provide a visual display of the image. Specifically, the MR signals fill or form a q-space that is reconstructed using the various methods described herein to obtain a viewable image. The processed signals representative of the image are then transmitted to the display device 728.

Various embodiments described herein provide a tangible and non-transitory machine-readable medium or media having instructions recorded thereon for a processor or computer to operate an imaging apparatus to perform an embodiment of a method described herein. The medium or media may be any type of CD-ROM, DVD, floppy disk, hard disk, optical disk, flash RAM drive, or other type of computer-readable medium or a combination thereof.

The various embodiments and/or components, for example, the monitor or display, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims..

What is claimed is:

1. A method for extracting a three-dimensional (3D) volume of interest from a three-dimensional (3D) image dataset, said method comprising:
   accessing a 3D image dataset that includes a plurality of image slices;
   enclosing a 3D volume of interest in the 3D image dataset using a 3D mesh, wherein the 3D mesh comprises a plurality of polygons;
   projecting the polygons onto two-dimensional (2D) planes;
   identifying, for each polygon, a set of 2D grid points that are bounded by the respective polygon;
   automatically extracting the 3D volume of interest based on the 3D mesh; and
   generating a 3D image of the extracted 3D volume of interest.

2. The method of claim 1, wherein the 3D mesh is configured to substantially encapsulate the object of interest.

3. The method of claim 1, wherein the plurality of polygons comprises a plurality of triangles, said method comprising:
   projecting the triangles onto three orthogonal two-dimensional (2D) planes; and
   identifying, for each triangle, a set of 2D grid points that are bounded by the respective triangle.

4. The method of claim 3, further comprising calculating a plurality of third-coordinates on a surface of the 3D mesh for each set of 2D grid points.

5. The method of claim 4, further comprising:
   creating an enclosed 3D surface on the 3D mesh using the third coordinates; and
   extracting the volume of interest using the enclosed 3D surface for each triangle.

6. The method of claim 1, further comprising:
   identifying image voxels that are within the 3D mesh;
   identifying image voxels that are outside the 3D mesh; and
   extracting the volume of interest using only the image voxels that are within the 3D mesh.

7. The method of claim 6, further comprising checking each image voxel in three orthogonal directions to determine if the surface point is inside or outside the 3D mesh.

8. The method of claim 1, further comprising displaying a 3D image of the 3D volume of interest and the 3D mesh on a display device.

9. A system for extracting a three-dimensional (3D) volume of interest from a three-dimensional (3D) image, said computer comprising:
   a user interface; and
   a processor coupled to the user interface, the processor being configured to:
   access a 3D image dataset that includes a plurality of image slices;
   enclose a 3Dvolume of interest in the 3D image dataset using a 3D mesh, wherein the 3D mesh comprises a plurality of polygons;
   project the polygons onto two-dimensional (2D) planes;
   identify, for each polygon, a set of 2D grid points that are bounded by the respective polygon;
   automatically extract the 3D volume of interest based on the 3D mesh; and
   generate a 3D image of the extracted 3D volume of interest.

10. The system of claim 9, wherein the 3D mesh is configured to substantially encapsulate the object of interest.

11. The system of claim 9, wherein the plurality of polygons comprises a plurality of triangles, said processor is further configured to:
    project the triangles onto three orthogonal two-dimensional (2D) planes; and
    identify, for each triangle, a set of 2D grid points that are bounded by the respective triangle.

12. The system of claim 9, wherein said processor is further configured to calculate a plurality of third-coordinates on a surface of the 3D mesh for each set of 2D grid points.

13. The system of claim 12, wherein said processor is further configured to:
    create an enclosed 3D surface on the 3D mesh using the third coordinates; and
    extract the volume of interest using the enclosed 3D surface for each triangle.

14. The system of claim 13, wherein said processor is further configured to:
    identify image voxels that are within the 3D mesh;
    identify image voxels that are outside the 3D mesh; and
    extract the volume of interest using only the image voxels that are within the 3D mesh.

15. The system of claim 14, wherein said processor is further configured to check each image voxel in three orthogonal directions to determine if the surface point is inside or outside the 3D mesh.

16. The system of claim 9, wherein said processor is further configured to display a 3D image of the 3D volume of interest and the 3D mesh on a display device.

17. A non-transitory computer readable medium programmed to instruct a computer to:
    access a 3D image dataset that includes a plurality of image slices;
    enclose a 3D volume of interest in the 3D image dataset using a 3D mesh, wherein the 3D mesh comprises a plurality of polygons;
    project the polygons onto two-dimensional (2D) planes;
    identify, for each polygon, a set of 2D grid points that are bounded by the respective polygon;
    automatically extract the 3D volume of interest based on the 3D mesh; and
    generate a 3D image of the extracted 3D volume of interest.

18. The non-transitory computer readable medium of claim 17, wherein the 3D mesh is configured to substantially encapsulate the object of interest.

19. The non-transitory computer readable medium of claim 17, wherein the plurality of polygons comprises a plurality of triangles, said computer readable medium further programmed to instruct a computer to:
    project the triangles onto three orthogonal two-dimensional (2D) planes; and
    identify, for each triangle, a set of 2D grid points that are bounded by the respective triangle.

20. The non-transitory computer readable medium of claim 17, wherein said computer readable medium is further programmed to instruct a computer to calculate a plurality of third-coordinates on a surface of the 3D mesh for each set of 2D grid points.

* * * * *